United States Patent
Kulkarni

(10) Patent No.: US 9,592,381 B2
(45) Date of Patent: Mar. 14, 2017

(54) SYSTEMS AND METHODS FOR FACILITATING SOUND LOCALIZATION BY A BILATERAL COCHLEAR IMPLANT PATIENT

(71) Applicant: ADVANCED BIONICS AG, Staefa (CH)

(72) Inventor: Abhijit Kulkarni, Newbury Park, CA (US)

(73) Assignee: Advanced Bionics AG, Staefa (CH)

( * ) Notice: Subject to any disclaimer, the term of this patent is extended or adjusted under 35 U.S.C. 154(b) by 67 days.

(21) Appl. No.: 14/437,186

(22) PCT Filed: Nov. 29, 2012

(86) PCT No.: PCT/US2012/067136
§ 371 (c)(1),
(2) Date: Apr. 20, 2015

(87) PCT Pub. No.: WO2014/065831
PCT Pub. Date: May 1, 2014

(65) Prior Publication Data
US 2015/0265837 A1 Sep. 24, 2015

Related U.S. Application Data

(60) Provisional application No. 61/717,781, filed on Oct. 24, 2012.

(51) Int. Cl.
*H04R 25/00* (2006.01)
*A61N 1/36* (2006.01)

(52) U.S. Cl.
CPC ........ *A61N 1/36032* (2013.01); *H04R 25/407* (2013.01); *H04R 25/552* (2013.01)

(58) Field of Classification Search
CPC ........ H04R 3/005; H04R 25/70; H04R 25/356; H04R 25/402; H04R 25/405;
(Continued)

(56) References Cited

U.S. PATENT DOCUMENTS

| 8,503,704 B2 * | 8/2013 | Francart ............ A61N 1/36032 381/312 |
| 2012/0070008 A1 | 3/2012 | Sohn et al. |
| 2012/0093329 A1 | 4/2012 | Francart et al. |

FOREIGN PATENT DOCUMENTS

| EP | 2563044 | 2/2013 |
| WO | WO-2010/115227 | 10/2010 |

OTHER PUBLICATIONS

International Search Report and Written Opinion received in International Application No. PCT/US12/067136, dated Oct. 22, 2013.

* cited by examiner

*Primary Examiner* — Brian Ensey
(74) *Attorney, Agent, or Firm* — ALG Intellectual Property, LLC

(57) ABSTRACT

An exemplary system for facilitating sound localization by a bilateral cochlear implant patient includes 1) a processing facility configured to determine an interaural difference between a first audio signal detected by a first microphone associated with a first ear of a bilateral cochlear implant patient and a second audio signal detected by a second microphone associated with a second ear of the bilateral cochlear implant patient and generate, based on the determined interaural difference, an enhanced interaural level difference (ILD) associated with the low frequency acoustic content of the first and second audio signals and 2) a control facility configured to direct a first cochlear implant associated with the first ear and a second cochlear implant associated with the second ear to generate electrical stimulation (Continued)

representative of the low frequency acoustic content in accordance with the enhanced ILD. Corresponding systems and methods are also disclosed.

20 Claims, 6 Drawing Sheets

SYSTEMS AND METHODS FOR FACILITATING SOUND LOCALIZATION BY A BILATERAL COCHLEAR IMPLANT PATIENT

RELATED APPLICATIONS

The present application claims priority to U.S. Provisional Patent Application No. 61/717,781 by Abhijit Kulkarni, filed on Oct. 24, 2012, and entitled "Systems and Methods for Facilitating Sound Localization by a Bilateral Cochlear Implant Patient," the contents of which are hereby incorporated by reference in their entirety.

BACKGROUND INFORMATION

People with normal hearing are able to localize sound (i.e., locate the direction of the source of the sound) by detecting various binaural cues with both ears. For example, sound originating from the right side of a person reaches the person's right before it reaches the person's left ear. The sound also has a higher level (i.e., amplitude) at the person's right ear than the person's left ear because the person's head shadows the left ear. These time and level differences as detected by the ears allow the person's auditory system to determine that the sound is coming from the person's right side.

Unfortunately, because sound localization requires the use of both ears, a unilateral cochlear implant patient (i.e., a person fitted with a cochlear implant in only one ear) is often incapable of localizing sound (assuming that the patient cannot hear with the non-implanted ear). Bilateral cochlear implant systems (i.e., systems in which a patient is fitted with a cochlear implant in both ears) have provided some degree of sound localization for cochlear implant patients. However, conventional cochlear implant systems have difficulty accurately representing binaural cues. Hence, the sound localization capabilities of bilateral cochlear implant patients are often quite poor.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
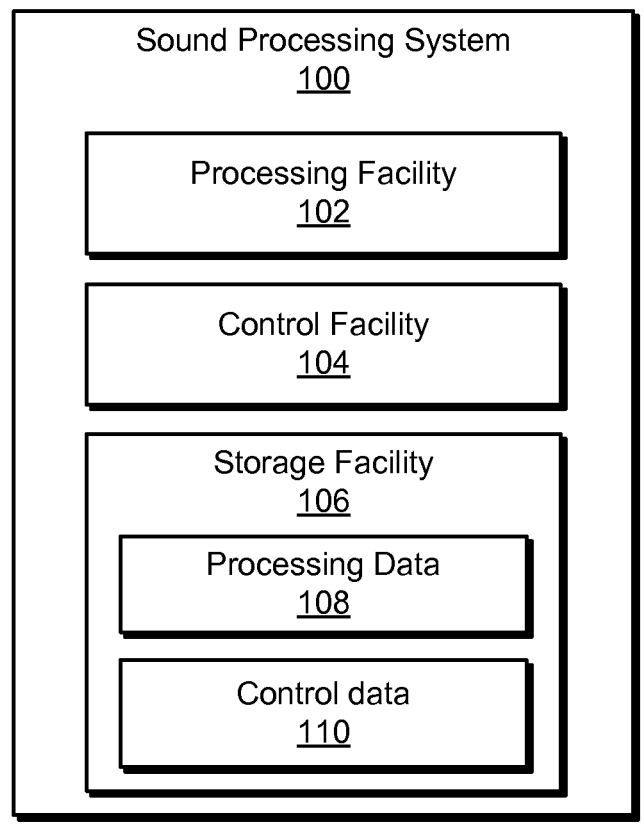
FIG. 1 illustrates an exemplary sound processing system according to principles described herein.

Systems and methods for facilitating sound localization by a bilateral cochlear implant patient are described herein.

As will be described below, a sound processing system may determine an interaural difference between a first audio signal detected by a first microphone associated with a first ear of a bilateral cochlear implant patient and a second audio signal detected by a second microphone associated with a second ear of the bilateral cochlear implant patient. The first and second audio signals may be representative of the same sound (i.e., generated by the same source) and may each include high frequency acoustic content above a predetermined frequency threshold (e.g., 1500 Hz) and low frequency acoustic content below the predetermined frequency threshold. The sound processing may then generate, based on the determined interaural difference, an enhanced interaural level difference ("ILD") associated with the low frequency acoustic content of the first and second audio signals and direct a first cochlear implant associated with the first ear of the bilateral cochlear implant patient and a second cochlear implant associated with the second ear of the bilateral cochlear implant patient to generate electrical stimulation representative of the low frequency acoustic content of the first and second audio signals in accordance with the enhanced ILD.

As used herein, an "interaural difference" between first and second audio signals refers to an ILD between the first and second audio signals, an interaural time difference ("ITD") between the first and second audio signals, and/or any other difference between the first and second audio signals that may be used as a binaural cue in sound localization. In some examples, the interaural difference between the first and second audio signals may be frequency-specific (e.g., associated only with the low frequency acoustic content contained within the first and second audio signals, only with the high frequency acoustic content contained within the first and second audio signals, or only with acoustic content contained within a particular analysis channel or frequency band).

As used herein, an "enhanced ILD" associated with the low frequency acoustic content of the first and second audio signals is an artificially determined ILD that is encoded into the low frequency acoustic content of the first and second audio signals by a bilateral cochlear implant system. The enhanced ILD may be generated in many different ways, as will be described below, and is, in many examples, greater than an original ILD associated with the low frequency acoustic content of the first and second audio signals (i.e., the ILD associated with the low frequency acoustic content of the first and second audio signals as detected originally by the first and second microphones).

The systems and methods described herein may enhance and/or improve sound localization by a bilateral cochlear implant patient compared to conventional cochlear implant systems for a variety of reasons. For example, binaural cues are acoustically encoded by way of time differences (i.e., ITDs) primarily present in the relatively low frequencies (e.g., frequencies less than 1500 Hz) and level differences (i.e., ILDs) primarily present in the relatively high frequencies (e.g., frequencies greater than 1500 Hz). ILD information is primarily processed within the brain by the lateral superior olive ("LSO"), which is connected to relatively high frequency auditory nerve fibers located within a basal region of the cochlea. ITD information, on the other hand, is primarily processed within the brain by the medial superior olive ("MSO"), which is connected to relatively low frequency auditory nerve fibers located within an apical region of the cochlea.

Studies have shown that bilateral cochlear implant patients are generally unable to show sensitivity to ITDs in sound stimulus. Sensitivity of bilateral cochlear implant patients to ILDs, on the other hand, has been demonstrated. Hence, it is largely believed that bilateral cochlear implant patients use ILD information to localize sound.

Unfortunately, a conventional cochlear implant system often presents conflicting ILD information to a cochlear implant patient, thereby preventing the patient from accurately localizing sound. This is because the electrode lead by way of which the conventional cochlear implant system applies electrical stimulation representative of the sound is often not fully inserted into the apical region of the cochlea in order to prevent causing structural damage to the cochlea. This, in turn, results in the electrodes responsible for conveying relatively low frequency acoustic content being in communication with relatively high frequency auditory nerve fibers disposed within the cochlea (instead of relatively low frequency auditory nerve fibers). Hence, relatively low frequency acoustic content conveyed by way of these electrodes is transmitted to the LSO instead of to the MSO. Because little (if any) ILD information is included in the relatively low frequency acoustic content, the ILD information (or lack thereof) included in the relatively low frequency acoustic content may conflict with the ILD information included in the relatively high frequency acoustic content concurrently processed by the LSO, thereby resulting in poor sound localization by the cochlear implant patient.

Hence, by encoding an artificially determined ILD into the low frequency acoustic content presented to the first and second ears of a bilateral cochlear implant patient, the systems and methods described herein may present consistent ILD information to the LSO of the patient. This, in turn, may result in the LSO providing a more robust percept of sound localization to the patient.

FIG. 1 illustrates an exemplary sound processing system 100 ("system 100"). As shown, system 100 may include, without limitation, a processing facility 102, a control facility 104, and a storage facility 106 communicatively coupled to one another. One or more of facilities 102-106 may include one or more computing devices and/or processors configured to perform one or more of the functions described herein. Facilities 102-106 will now be described in more detail.

Processing facility 102 may be configured to perform one or more processing operations with respect to audio signals detected by first and second microphones included within a bilateral cochlear implant system. For example, processing facility 102 may determine an interaural difference between a first audio signal detected by a first microphone associated with a first ear (e.g., a left ear) of a bilateral cochlear implant patient and a second audio signal detected by a second microphone associated with a second ear (e.g., a right ear) of the bilateral cochlear implant patient.

Figure 2:
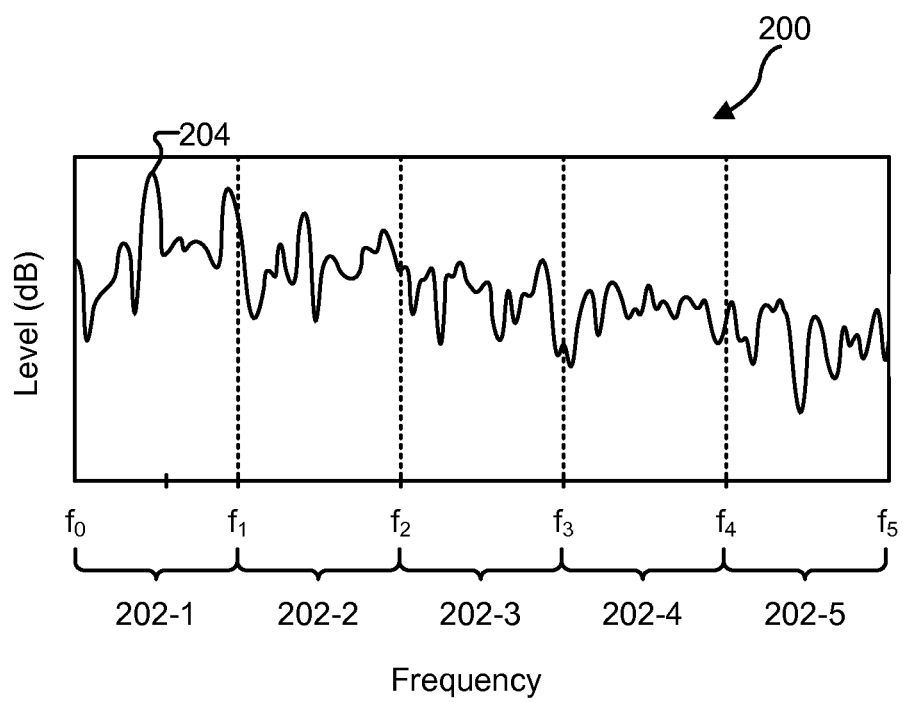
FIG. 2 shows a graph of an exemplary audio signal according to principles described herein.

As mentioned, the first and second audio signals may each include high frequency acoustic content above a predetermined frequency threshold and low frequency acoustic content below the predetermined frequency threshold. To illustrate, FIG. 2 shows a graph 200 of an exemplary audio signal that may be detected by the first and/or second microphones. As shown, the audio signal may be divided into a plurality of analysis channels 202 (e.g., analysis channels 202-1 through 202-5). Each analysis channel 202 may correspond to a particular frequency band. For example, analysis channel 202-1 corresponds to a frequency band defined by frequencies $f_0$ and $f_1$, analysis channel 202-2 corresponds to a frequency band defined by frequencies $f_1$ and $f_2$, etc.

Processing facility 102 may divide the audio signal into analysis channels 202 in any suitable manner. For example, processing facility 102 may include a plurality of band-pass filters configured to divide the audio signal into a plurality of frequency channels or bands. Additionally or alternatively, processing facility 102 may be configured to convert the audio signals from a time domain into a frequency domain and then divide the resulting frequency bins into the analysis channels. To this end, processing facility 102 may apply a Discrete Fourier Transform (e.g., a Fast Fourier Transform ("FFT")) to the audio signals.

As shown, each analysis channel 202 may contain acoustic content (e.g., spectral content associated with the audio signal) represented by curve 204. While acoustic content is shown to be included in each analysis channel 202, it will be recognized that in some cases, a particular analysis channel may not include any acoustic content.

The predetermined frequency threshold above which acoustic content is referred to herein as "high frequency acoustic content" and below which acoustic content is referred to herein as "low frequency acoustic content" may be set and/or otherwise determined in any suitable manner. For example, the predetermined frequency threshold may be set such that one or more entire analysis channels (e.g., analysis channels 202-1 and 202-2) are below the predetermined frequency threshold. To illustrate, referring to FIG. 2, the predetermined frequency threshold may be set to be equal to $f_2$. As mentioned, an exemplary predetermined frequency threshold is 1500 Hz.

Processing facility 102 may determine the interaural difference between the first and second audio signals in any suitable manner. For example, processing facility 102 may compute a level difference (e.g., an ILD) between the first and second audio signals, a time difference (e.g., an ITD) between the first and second audio signals, and/or any other difference between the first and second audio signals as may serve a particular implementation.

As mentioned, the interaural difference between the first and second audio signals may be frequency-specific. For example, the interaural difference between the first and second audio signals may be associated only with the low frequency acoustic content contained within the first and second audio signals. In this example, processing facility 102 may determine the interaural difference by computing an ILD, ITD, and/or any other interaural difference between the low frequency acoustic content contained within the first audio signal and the low frequency acoustic content contained within the second audio signal.

As another example, the interaural difference between the first and second audio signals may be associated only with the high frequency acoustic content contained within the first and second audio signals. In this example, processing facility 102 may determine the interaural difference by computing an ILD, ITD, and/or any other interaural difference between the high frequency acoustic content contained within the first audio signal and the high frequency acoustic content contained within the second audio signal.

As another example, the interaural difference between the first and second audio signals may be associated only with acoustic content contained within a particular analysis channel (e.g., analysis channel 202-1) of the first and second audio signals. In this example, processing facility 102 may determine the interaural difference by computing an ILD, ITD, and/or any other interaural difference between the acoustic content contained within the particular analysis channel of first audio signal and the acoustic content contained within the particular analysis channel of the second audio signal.

Processing facility 102 may be further configured to generate, based on the determined interaural difference, an enhanced ILD associated with the low frequency acoustic content of the first and second audio signals. As will be described below, the enhanced ILD may be encoded into the low frequency acoustic content of the first and second audio signals in order to facilitate sound localization by a bilateral cochlear implant patient.

Processing facility 102 may generate the enhanced ILD based on the determined interaural difference in any suitable manner. For example, processing facility 102 may generate the enhanced ILD by selecting the enhanced ILD from a look-up table that defines a relationship between a plurality of interaural differences and a plurality of enhanced ILDs.

Figure 3:
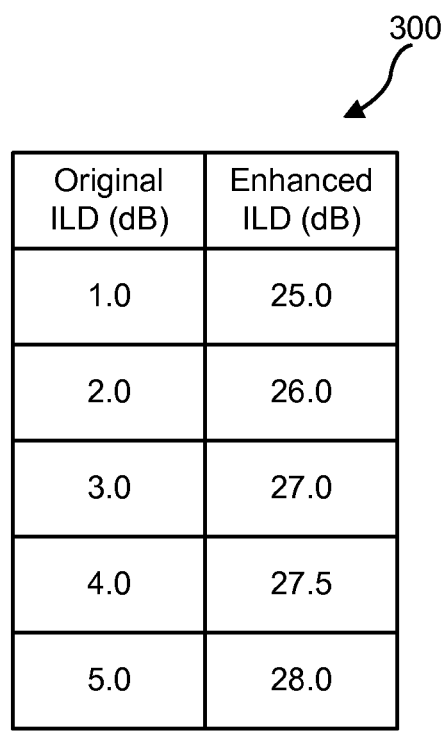
FIG. 3 shows an exemplary look-up table that may be used to generate an enhanced ILD associated with low frequency acoustic content of first and second audio signals according to principles described herein.

To illustrate, FIG. 3 shows an exemplary look-up table 300 that may be maintained by processing facility 102 and that may be used by processing facility 102 to generate an enhanced ILD associated with the low frequency acoustic content of the first and second audio signals. As shown, look-up table 300 defines a relationship between a plurality of original ILDs associated with the low frequency acoustic content of the first and second audio signals and a plurality of enhanced ILDs associated with the low frequency acoustic content of the first and second audio signals.

Processing facility 102 may utilize look-up table 300 by first determining an original ILD associated with the low frequency acoustic content of the first and second audio signals, locating the original ILD within look-up table 300, and selecting the an enhanced ILD that corresponds to the original ILD from look-up table 300. To illustrate, processing facility 102 may determine that an original ILD associated with the low frequency acoustic content of the first and second audio signals is 3.0 dB. Processing facility 102 may then select, based on look-up table 300, a value of 27.0 dB as the enhanced ILD to be associated with the low frequency acoustic content of the first and second audio signals.

Additionally or alternatively, processing facility 102 may generate the enhanced ILD associated with the low frequency acoustic content of the first and second audio signals by using any predetermined parametric formula. For example, the determined interaural difference between the first and second audio signals may be the original ILD associated with the low frequency acoustic content of the first and second audio signals. In this example, processing facility 102 may generate the enhanced ILD in accordance with the following parametric formula: $ILD_{enhanced\_low} = F(ILD_{original\_low})$. In other words, the enhanced ILD of the low frequency acoustic content (i.e., $ILD_{enhanced\_low}$) is a function of the original ILD of the low frequency acoustic content (i.e., $ILD_{original\_low}$). To illustrate, processing facility 102 may be configured to generate the enhanced ILD associated with the low frequency acoustic content by adding a predetermined amount (e.g., 20 dB) to the original ILD associated with the low frequency acoustic content.

As another example, the determined interaural difference between the first and second audio signals may be an original ILD associated with the high frequency acoustic content of the first and second audio signals. In this example, processing facility 102 may generate the enhanced ILD in accordance with the following parametric formula: $ILD_{enhanced\_low} = F(ILD_{original\_high})$. In other words, the enhanced ILD of the low frequency acoustic content (i.e., $ILD_{enhanced\_low}$) is a function of the original ILD of the low frequency acoustic content (i.e., $ILD_{original\_high}$). To illustrate, processing facility 102 may be configured to generate the enhanced ILD associated with the low frequency acoustic content by setting the enhanced ILD of the low frequency acoustic content to be substantially equal to the original ILD of the high-frequency acoustic content. In this manner, the ILD of the low frequency acoustic content may be artificially enhanced to mimic the ILD of the high frequency acoustic content.

Additionally or alternatively, the enhanced ILD associated with the low frequency acoustic content of the first and second audio signals may be generated as a function of an ITD associated with the low frequency acoustic content of the first and second audio signals. For example, processing facility 102 may generate the enhanced ILD by selecting an ILD that is proportional to the ITD associated with the low frequency acoustic content as the enhanced ILD. To illustrate, processing facility 102 may generate the enhanced ILD in accordance with the following equation: $ILD_{enhanced\_low} = k*(ITD_{original\_low})$. In this equation, $ILD_{enhanced\_low}$ represents the enhanced ILD associated with the low frequency acoustic content of the first and second audio signals, $ITD_{original\_low}$ represents the original ITD associated with the low frequency acoustic content of the first and second audio signals as determined by processing facility 102, and k represents a multiplication factor that may be set automatically by processing facility 102, in response to manual input (e.g., input provided by a clinician or other user), or in any other manner as may serve a particular implementation).

Returning to FIG. 1, control facility 104 may be configured to perform one or more cochlear implant control operations as may serve a particular implementation. For example, control facility 104 may direct a first cochlear implant associated with the first ear of the bilateral cochlear implant patient and a second cochlear implant associated with the second ear of the bilateral cochlear implant patient to generate electrical stimulation representative of the low frequency acoustic content of the first and second audio signals in accordance with the enhanced ILD generated by processing facility 104. This may be performed any suitable manner.

For example, control facility 104 may direct the first and second cochlear implants to generate the electrical stimulation representative of the low frequency acoustic content of the first and second audio signals in accordance with the enhanced ILD by encoding data representative of the enhanced ILD into data representative of the low frequency acoustic content of the first and second audio signals and directing the first and second cochlear implants to generate the electrical stimulation in accordance with the data representative of the low frequency acoustic content that has been encoded with the data representative of the enhanced ILD. Control facility 104 may be further configured to direct the first and second cochlear implants to apply the electrical stimulation representative of the low frequency acoustic content of the first and second audio signals in accordance with the enhanced ILD by way of one or more electrodes associated with one or more analysis channels located below the predetermined frequency threshold.

To illustrate, control facility 104 may encode data representative of the enhanced ILD into data representative of the low frequency acoustic content of the first and second audio signals by setting one or more stimulation parameters that specify the amplitude of the electrical stimulation that is to be generated and applied by the first and second cochlear implants. This may be performed in any suitable manner. For example, control facility 104 may set one or more stimulation parameters that direct the first cochlear implant to generate a first stimulation signal having a first amplitude and that is representative of the low frequency acoustic content of the first audio signal. Control facility 104 may also set one or more stimulation parameters that direct the second cochlear implant to generate a second stimulation signal having a second amplitude and that is representative of the low frequency acoustic content of the second audio signal. Control facility 104 may set the first and second amplitudes such that the difference between the first and second amplitudes is defined by (i.e., substantially equal to) the enhanced ILD.

Storage facility 106 may be configured to maintain processing data 108 generated and/or used by processing facility 102 and/or control data 110 generated and/or used by control facility 104. It will be recognized that storage facility 106 may maintain additional or alternative data as may serve a particular implementation.

Figure 4:
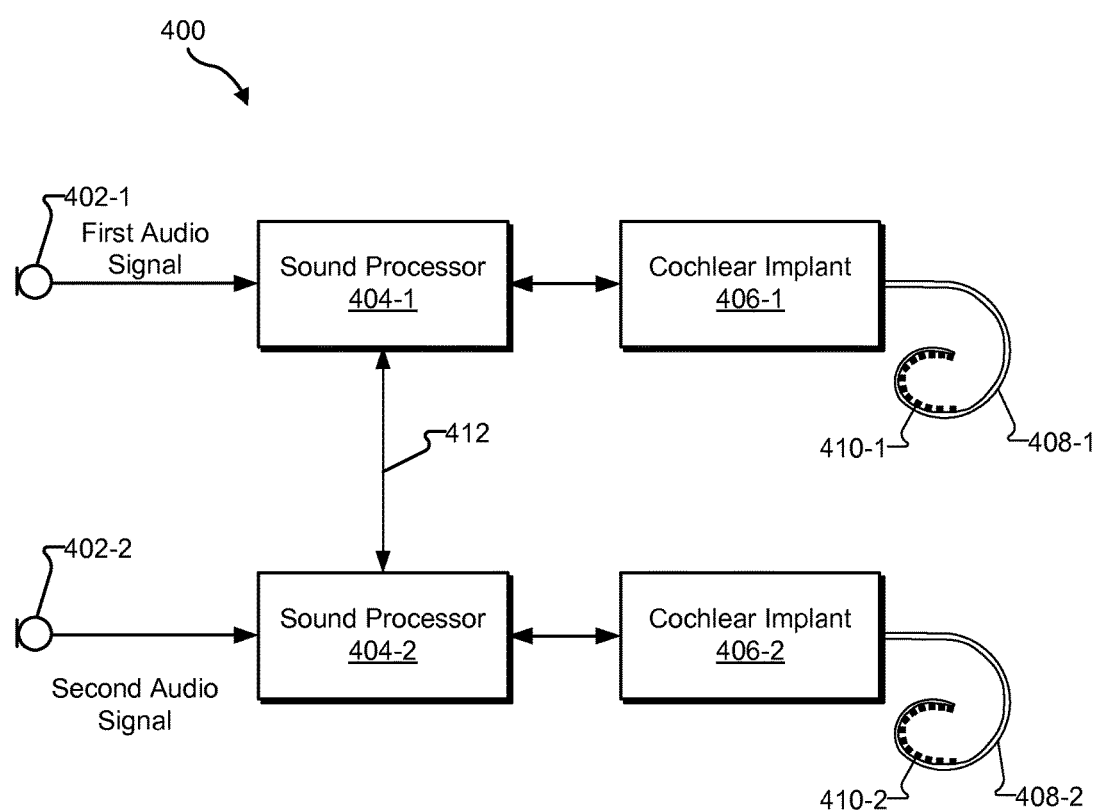
FIG. 4 illustrates an exemplary bilateral cochlear implant system according to principles described herein.

FIG. 4 illustrates an exemplary bilateral cochlear implant system 400 that may be used in connection with the systems and methods described herein. As shown, bilateral cochlear implant system 400 may include first and second microphones 402-1 and 402-2 (collectively "microphones 402"), first and second sound processors 404-1 and 404-2 (collectively "sound processors 404"), cochlear implants 406-1 and 406-2 (collectively "cochlear implants 406"), and electrode leads 408-1 and 408-2 (collectively "electrode leads 408"), each having electrodes 410 (e.g., electrodes 410-1 and 410-2) disposed thereon. Microphone 402-1, sound processor 404-1, cochlear implant 406-1, electrode lead 408-1 and electrodes 410-1 are associated with a first ear (e.g., the left ear) of the patient and microphone 402-2, sound processor 404-2, cochlear implant 406-2, electrode lead 408-2 and electrodes 410-2 are associated with a second ear (e.g., the right ear) of the patient.

Microphones 402 may be configured to detect first and second audio signals (e.g., audio signals representative of the same sound) presented to the left and right ears of the patient, respectively. For example, first microphone 402-1 may be positioned proximal to the left ear canal of the patient and second microphone 402-2 may be positioned proximal to the right ear canal of the patient. Various other microphone arrangements may be used in connection with the systems and methods described herein.

Sound processors 404 may each include any suitable device configured to process the first and second audio signals detected by microphones 402. In some examples, each sound processor 404 is implemented by an externally worn unit (e.g., a behind-the-ear device, a body worn device, etc.). Alternatively, each sound processor 404 may be configured to be at least partially implanted within the patient. One or more facilities included in system 100 may be implemented by sound processors 404.

Sound processors 404-1 and 404-2 may be communicatively coupled to microphones 402-1 and 402-2, respectively, in any suitable manner as may serve a particular implementation. For example, sound processors 404-1 and 404-2 may be communicatively coupled to microphones 402-1 and 402-2, respectively, using a wired and/or wireless connection. Likewise, sound processors 404-1 and 404-2 may be communicatively coupled to cochlear implants 406-1 and 406-2, respectively, in any suitable manner as may serve a particular implementation. For example, sound processors 404-1 and 404-2 may be communicatively coupled to cochlear implants 406-1 and 406-2, respectively, using a wired and/or wireless connection.

As shown, sound processors 404-1 and 404-2 may be configured to communicate by way of communication channel 412, which may be wired or wireless as may serve a particular implementation. In this manner, each facility included in system 100 may be implemented by sound processor 404-1, sound processor 404-2, and/or a combination thereof. For example, sound processor 404-1 may be configured to transmit level and/or timing data associated with the first audio signal to sound processor 404-2, which may utilize the data together with level and/or timing data associated with the second audio signal that sound processor 404-2 detects to determine an interaural difference between the first and second audio signals. Sound processor 404-2 may then generate an enhanced ILD based on the determined interaural difference and transmit data to sound processor 404-1 representative of or otherwise associated with the enhanced ILD so that sound processor 404-1 may direct cochlear implant 406-1 to generate electrical stimulation in accordance with the enhanced ILD.

Cochlear implants 406 may each include any suitable auditory prosthesis configured to be at least partially implanted within a patient as may serve a particular implementation. For example, cochlear implants 406 may each include an implantable cochlear stimulator, a brainstem implant and/or any other type of auditory prosthesis.

Electrode leads 408 may be implanted within the patient such that electrodes 410 are in communication with stimulation sites within the cochlea and/or anywhere else along the auditory pathway of the patient. In this configuration, sound processors 404 may direct cochlear implants 406 to apply electrical stimulation representative of first and second audio signals to one or more stimulation sites within the patient by way of one or more stimulation channels formed by electrodes 410.

Figure 5:
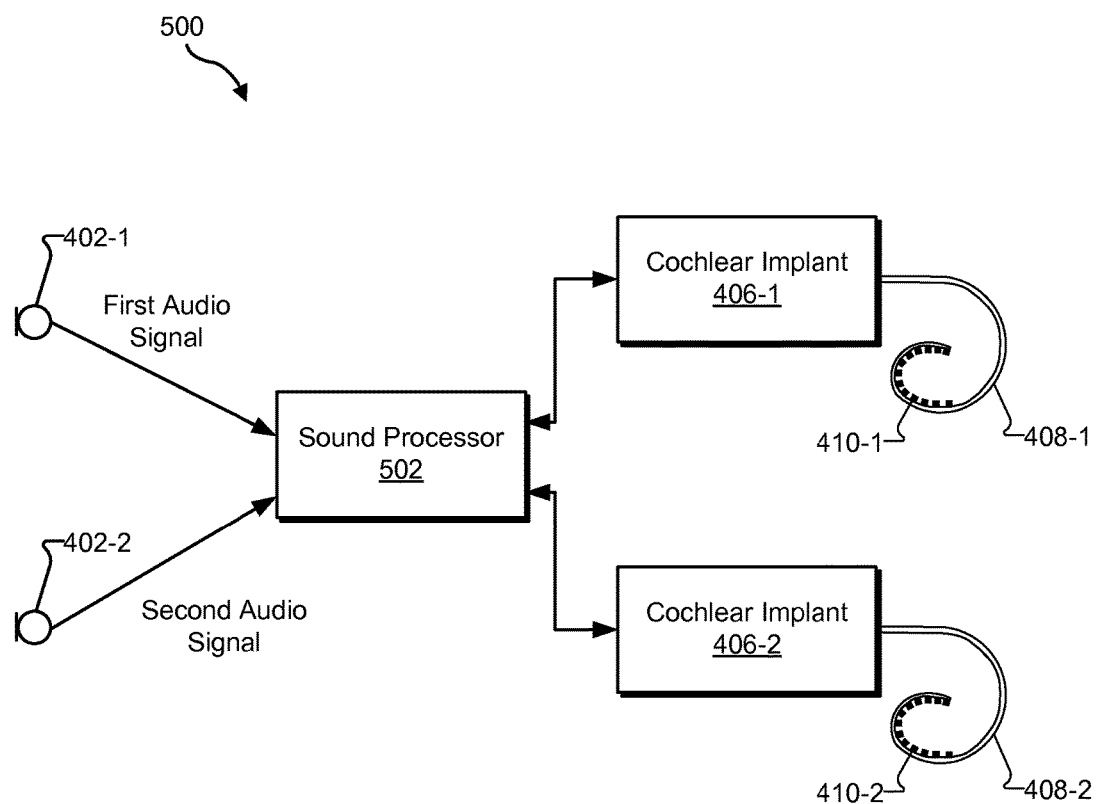
FIG. 5 illustrates another exemplary bilateral cochlear implant system according to principles described herein.

FIG. 5 illustrates another exemplary bilateral cochlear implant system 500 that may be used in connection with the systems and methods described herein. As shown, bilateral cochlear implant system 500 is similar to bilateral cochlear implant system 500 in that it includes microphones 402, cochlear implants 406, electrode leads 408, and electrodes 410. However, bilateral cochlear implant system 500 includes a single sound processor 502 configured to process both first and second audio signals detected by microphones 402 and to control both cochlear implants 406. Sound processor 502 may be implemented by any of the sound processors described herein.

Figure 6:
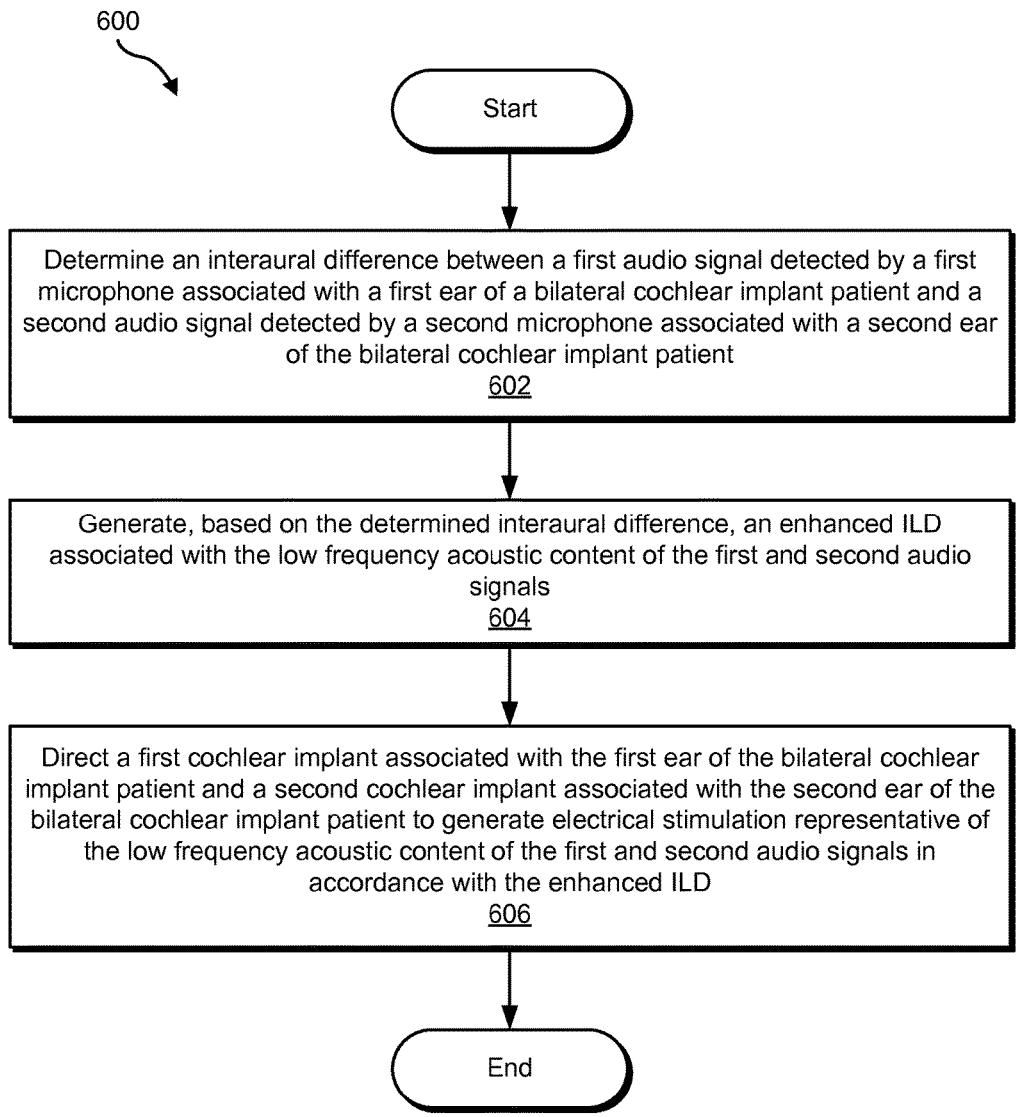
FIG. 6 illustrates an exemplary method of facilitating sound localization by a bilateral cochlear implant patient according to principles described herein.

FIG. 6 illustrates an exemplary method 600 of facilitating sound localization by a bilateral cochlear implant patient. While FIG. 6 illustrates exemplary steps according to one embodiment, other embodiments may omit, add to, reorder, and/or modify any of the steps shown in FIG. 6. One or more of the steps shown in FIG. 6 may be performed by system 100 and/or any implementation thereof.

In step 602, a sound processing system determines an interaural difference between a first audio signal detected by a first microphone associated with a first ear of a bilateral cochlear implant patient and a second audio signal detected by a second microphone associated with a second ear of the bilateral cochlear implant patient. As described above, the first and second audio signals may each include high frequency acoustic content above a predetermined frequency threshold and low frequency acoustic content below the predetermined frequency threshold. Step 602 may be performed in any of the ways described herein.

In step 604, the sound processing system generates, based on the determined interaural difference, an enhanced ILD associated with the low frequency acoustic content of the first and second audio signals. Step 604 may be performed in any of the ways described herein.

In step 606, the sound processing system directs a first cochlear implant associated with the first ear of the bilateral cochlear implant patient and a second cochlear implant associated with the second ear of the bilateral cochlear implant patient to generate electrical stimulation representative of the low frequency acoustic content of the first and second audio signals in accordance with the enhanced ILD. Step 606 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a processing facility configured to
determine an interaural difference between a first audio signal detected by a first microphone associated with a first ear of a bilateral cochlear implant patient and a second audio signal detected by a second microphone associated with a second ear of the bilateral cochlear implant patient, the first and second audio signals each including high frequency acoustic content above a predetermined frequency threshold and low frequency acoustic content below the predetermined frequency threshold, and
generate, based on the determined interaural difference, an enhanced interaural level difference ("ILD") associated with the low frequency acoustic content of the first and second audio signals; and
a control facility communicatively coupled to the processing facility and configured to direct a first cochlear implant associated with the first ear of the bilateral cochlear implant patient and a second cochlear implant associated with the second ear of the bilateral cochlear implant patient to generate electrical stimulation representative of the low frequency acoustic content of the first and second audio signals in accordance with the enhanced ILD by:
directing the first cochlear implant to generate a first stimulation signal representative of the low frequency acoustic content of the first audio signal and having a first amplitude, and
directing the second cochlear implant to generate a second stimulation signal representative of the low frequency acoustic content of the second audio signal and having a second amplitude;
wherein a difference between the first and second amplitudes is defined by the enhanced ILD.

2. The system of claim 1, wherein the control facility is further configured to direct the first and second cochlear implants to generate the electrical stimulation representative of the low frequency acoustic content of the first and second audio signals in accordance with the enhanced ILD by:
encoding data representative of the enhanced ILD into data representative of the low frequency acoustic content of the first and second audio signals; and
directing the first and second cochlear implants to generate the electrical stimulation in accordance with the data representative of the low frequency acoustic content that has been encoded with the data representative of the enhanced ILD.

3. The system of claim 1, wherein the processing facility is configured to generate the enhanced ILD by selecting the enhanced ILD from a look-up table that defines a relationship between a plurality of interaural differences and a plurality of enhanced ILDs.

4. The system of claim 1, wherein:
the determined interaural difference between the first and second audio signals is an original ILD associated with the low frequency acoustic content of the first and second audio signals; and
the processing facility is configured to generate the enhanced ILD as a function of the original ILD.

5. The system of claim 1, wherein:
the determined interaural difference between the first and second audio signals is an original ILD associated with the low frequency acoustic content of the first and second audio signals; and
the processing facility is configured to generate the enhanced ILD by adding a predetermined amount to the original ILD.

6. The system of claim 1, wherein:
the determined interaural difference between the first and second audio signals is an ILD associated with the high frequency acoustic content of the first and second audio signals; and
the processing facility is configured to generate the enhanced ILD by setting the enhanced ILD to be substantially equal to the ILD associated with the high frequency content.

7. The system of claim 1, wherein:
the determined interaural difference between the first and second audio signals is an ILD associated with the high frequency acoustic content of the first and second audio signals; and
the processing facility is configured to generate the enhanced ILD as a function of the ILD associated with the high frequency content.

8. The system of claim 1, wherein:
the determined interaural difference between the first and second audio signals is an interaural time difference ("ITD") associated with the low frequency acoustic content of the first and second audio signals; and
the processing facility is configured to generate the enhanced ILD by selecting an ILD that is proportional to the ITD as the enhanced ILD.

9. The system of claim 1, wherein the enhanced ILD is greater than an ILD associated with the low frequency acoustic content of the first and second audio signals.

10. A system comprising:
a processing facility configured to
determine an interaural difference between a first audio signal detected by a first microphone associated with a first ear of a bilateral cochlear implant patient and a second audio signal detected by a second microphone with a second ear of the bilateral cochlear implant patient, the first and second audio signals each including high frequency acoustic content above a predetermined frequency threshold and low frequency acoustic content below the predetermined frequency threshold, and
generate, based on the determined interaural difference, an enhanced interaural level difference ("ILD") associated with the low frequency acoustic content of the first and second audio signals; and a control facility communicatively coupled to the processing facility and configured to direct a first cochlear implant associated with the first ear of the bilateral cochlear implant patient and a second cochlear implant associated with the second ear of the bilateral cochlear implant patient to:

generate electrical stimulation representative of the low frequency acoustic content of the first and second audio signals in accordance with the enhanced ILD, and apply the electrical stimulation representative of the low frequency acoustic content of the first and second audio signals in accordance with the enhanced ILD by way of electrodes associated with analysis channels located below the predetermined frequency threshold.

11. The system of claim 1, wherein the predetermined frequency threshold is substantially equal to 1500 Hz.

12. A system comprising:

a first microphone associated with a first ear of a cochlear implant patient and configured to detect a first audio signal presented to the first ear;

a second microphone associated with a second ear of the patient and configured to detect a second audio signal presented to the second ear, the first and second audio signals each including high frequency acoustic content above a predetermined frequency threshold and low frequency acoustic content below the predetermined frequency threshold; and a sound processor communicatively coupled to the first and second microphones and configured to determine an interaural difference between the first and second audio signals, generate, based on the determined interaural difference, an enhanced interaural level difference ("ILD") associated with the low frequency acoustic content of the first and second audio signals, and direct a first cochlear implant associated with the first ear of the bilateral cochlear implant patient and a second cochlear implant associated with the second ear of the bilateral cochlear implant patient to generate electrical stimulation representative of the low frequency acoustic content of the first and second audio signals in accordance with the enhanced ILD by:

directing the first cochlear implant to generate a first stimulation signal representative of the low frequency acoustic content of the first audio signal and having a first amplitude, and directing the second cochlear implant to generate a second stimulation signal representative of the low frequency acoustic content of the second audio signal and having a second amplitude;

wherein a difference between the first and second amplitudes is defined by the enhanced ILD.

13. A method comprising:

determining, by a sound processing system, an interaural difference between a first audio signal detected by a first microphone associated with a first ear of a bilateral cochlear implant patient and a second audio signal detected by a second microphone associated with a second ear of the bilateral cochlear implant patient, the first and second audio signals each including high frequency acoustic content above a predetermined frequency threshold and low frequency acoustic content below the predetermined frequency threshold;

generating, by the sound processing system based on the determined interaural difference, an enhanced interaural level difference ("ILD") associated with the low frequency acoustic content of the first and second audio signals; and directing, by the sound processing system, a first cochlear implant associated with the first ear of the bilateral cochlear implant patient and a second cochlear implant associated with the second ear of the bilateral cochlear implant patient to generate electrical stimulation representative of the low frequency acoustic content of the first and second audio signals in accordance with the enhanced ILD, wherein the directing of the first and second cochlear implants to generate the electrical stimulation representative of the low frequency acoustic content of the first and second audio signals in accordance with the enhanced ILD comprises:

directing the first cochlear implant to generate a first stimulation signal representative of the low frequency acoustic content of the first audio signal and having a first amplitude, and directing the second cochlear implant to generate a second stimulation signal representative of the low frequency acoustic content of the second audio signal and having a second amplitude;

wherein a difference between the first and second amplitudes is defined by the enhanced ILD.

14. The method of claim 13, wherein the directing of the first and second cochlear implants to generate the electrical stimulation representative of the low frequency acoustic content of the first and second audio signals in accordance with the enhanced ILD further comprises:

encoding data representative of the enhanced ILD into data representative of the low frequency acoustic content of the first and second audio signals; and directing the first and second cochlear implants to generate the electrical stimulation in accordance with the data representative of the low frequency acoustic content that has been encoded with the data representative of the enhanced ILD.

15. The method of claim 13, wherein the generating comprises selecting the enhanced ILD from a look-up table that defines a relationship between a plurality of interaural differences and a plurality of enhanced ILDs.

16. The method of claim 13, wherein:

the determined interaural difference between the first and second audio signals is an original ILD associated with the low frequency acoustic content of the first and second audio signals; and the generating comprises generating the enhanced ILD as a function of the original ILD.

17. The method of claim 13, wherein:

the determined interaural difference between the first and second audio signals is an ILD associated with the high frequency acoustic content of the first and second audio signals; and the generating comprises generating the enhanced ILD by setting the enhanced ILD to be substantially equal to the ILD associated with the high frequency content.

18. The method of claim 13, wherein:

the determined interaural difference between the first and second audio signals is an interaural time difference ("ITD") associated with the low frequency acoustic content of the first and second audio signals; and the generating comprises generating the enhanced ILD by selecting an ILD that is proportional to the ITD as the enhanced ILD.

19. The system of claim 1, wherein the control facility is further configured to direct the first and second cochlear implants to apply the electrical stimulation representative of the low frequency acoustic content of the first and second audio signals in accordance with the enhanced ILD by way of electrodes associated with analysis channels located below the predetermined frequency threshold.

20. The method of claim 13, further comprising directing, by the sound processing system, the first and second cochlear implants to apply the electrical stimulation representative of the low frequency acoustic content of the first and second audio signals in accordance with the enhanced ILD by way of electrodes associated with analysis channels located below the predetermined frequency threshold.

* * * * *